US012595218B2

(12) United States Patent
Mathur et al.

(10) Patent No.: US 12,595,218 B2
(45) Date of Patent: Apr. 7, 2026

(54) PROCESS FOR CONVERTING OLEFINS TO DISTILLATE FUELS WITH OLIGOMERATE RECYCLE

(71) Applicant: UOP LLC, Des Plaines, IL (US)

(72) Inventors: Ashish Mathur, Gurgaon (IN); Manuela Serban, Northbrook, IL (US); Joel S. Paustian, Vernon Hills, IL (US); Deng-Yang Jan, Elk Grove Village, IL (US)

(73) Assignee: UOP LLC, Rosemont, IL (US)

( * ) Notice: Subject to any disclaimer, the term of this patent is extended or adjusted under 35 U.S.C. 154(b) by 116 days.

(21) Appl. No.: 18/238,686

(22) Filed: Aug. 28, 2023

(65) Prior Publication Data
US 2024/0067586 A1     Feb. 29, 2024

(30) Foreign Application Priority Data

| | | | |
|---|---|---|---|
| Aug. 30, 2022 | (IN) | ............................... | 202211049522 |
| Aug. 30, 2022 | (IN) | ............................... | 202211049524 |
| Aug. 30, 2022 | (IN) | ............................... | 202211049525 |

(51) Int. Cl.
*C07C 2/12*          (2006.01)

(52) U.S. Cl.
CPC .......... *C07C 2/12* (2013.01); *C07C 2523/755* (2013.01); *C07C 2529/70* (2013.01)

(58) Field of Classification Search
None
See application file for complete search history.

(56) References Cited

U.S. PATENT DOCUMENTS

| | | | | |
|---|---|---|---|---|
| 4,740,645 | A * | 4/1988 | Garwood | ................ C07C 11/02 585/329 |
| 9,932,531 | B2 | 4/2018 | Lilga et al. | |
| 9,957,449 | B2 | 5/2018 | Luebke et al. | |
| 2007/0049781 | A1* | 3/2007 | Brown | .................... C10G 50/00 422/138 |
| 2011/0275871 | A1* | 11/2011 | Sanchez | .................... C07C 2/24 585/323 |
| 2011/0313221 | A1* | 12/2011 | Guillon | .................... C10G 3/49 585/324 |
| 2014/0135543 | A1 | 5/2014 | Nicholas et al. | |
| 2014/0135547 | A1 | 5/2014 | Nicholas et al. | |
| 2014/0249340 | A1* | 9/2014 | Tom | ....................... C10G 50/00 585/255 |
| 2015/0166424 | A1* | 6/2015 | Vanden Bussche | ... C10G 57/02 585/300 |
| 2015/0246855 | A1* | 9/2015 | Vivien | ................... C10G 45/00 585/254 |
| 2021/0129121 | A1 | 5/2021 | Gounder et al. | |

OTHER PUBLICATIONS

Search Report and Written Opinion for PCT/US2023/073177 dated Dec. 26, 2023.

* cited by examiner

*Primary Examiner* — Ali Z Fadhel

(74) *Attorney, Agent, or Firm* — Paschall & Associates, LLC; James C. Paschall

(57) ABSTRACT

A process for dimerizing and oligomerizing olefins to distillate fuels which utilizes a solid acid catalyst for ethylene oligomerization in a first stage and a metal catalyst for further oligomerization in a second stage. Distillate fuels can be produced from the process. Oligomerized olefins may be recycled to the first stage oligomerization reaction to ensure sufficient oligomerization of smaller olefins.

10 Claims, 4 Drawing Sheets

PROCESS FOR CONVERTING OLEFINS TO DISTILLATE FUELS WITH OLIGOMERATE RECYCLE

FIELD

The field is the conversion of olefins to distillate. The field may particularly relate to oligomerizing olefins and oligomerizing the oligomerized olefins to distillate fuels.

BACKGROUND

Ethylene can be oligomerized into olefins such as C4, C6 and C8 olefins. Olefin oligomerization is a process that can oligomerize smaller olefins into larger olefins. More specifically, it can convert olefins including oligomerized olefins into distillates including jet fuel and diesel range products. The oligomerized distillate can be saturated for use as transportation fuels.

The dimerization reaction of ethylene is highly exothermic. The exotherm generated by ethylene dimerization can be difficult to manage.

Jet fuel is one of the few petroleum fuels that cannot be replaced easily by electrical motor systems because a high energy density is required to fuel planes which cannot be supplied with batteries. Large incentives are currently available for green jet fuel in certain regions.

An efficient process is desired for converting ethylene to distillate fuels.

BRIEF SUMMARY

We have formulated a process for oligomerizing olefins to distillate fuels which utilizes a zeolitic catalyst for ethylene in the first stage oligomerization and a metal catalyst for oligomer olefins in a second stage oligomerization.

We have also formulated a process for oligomerizing olefins to distillate fuels which recycles oligomerized olefins to a downstream first stage oligomerization catalyst bed.

DEFINITIONS

Figure 1:
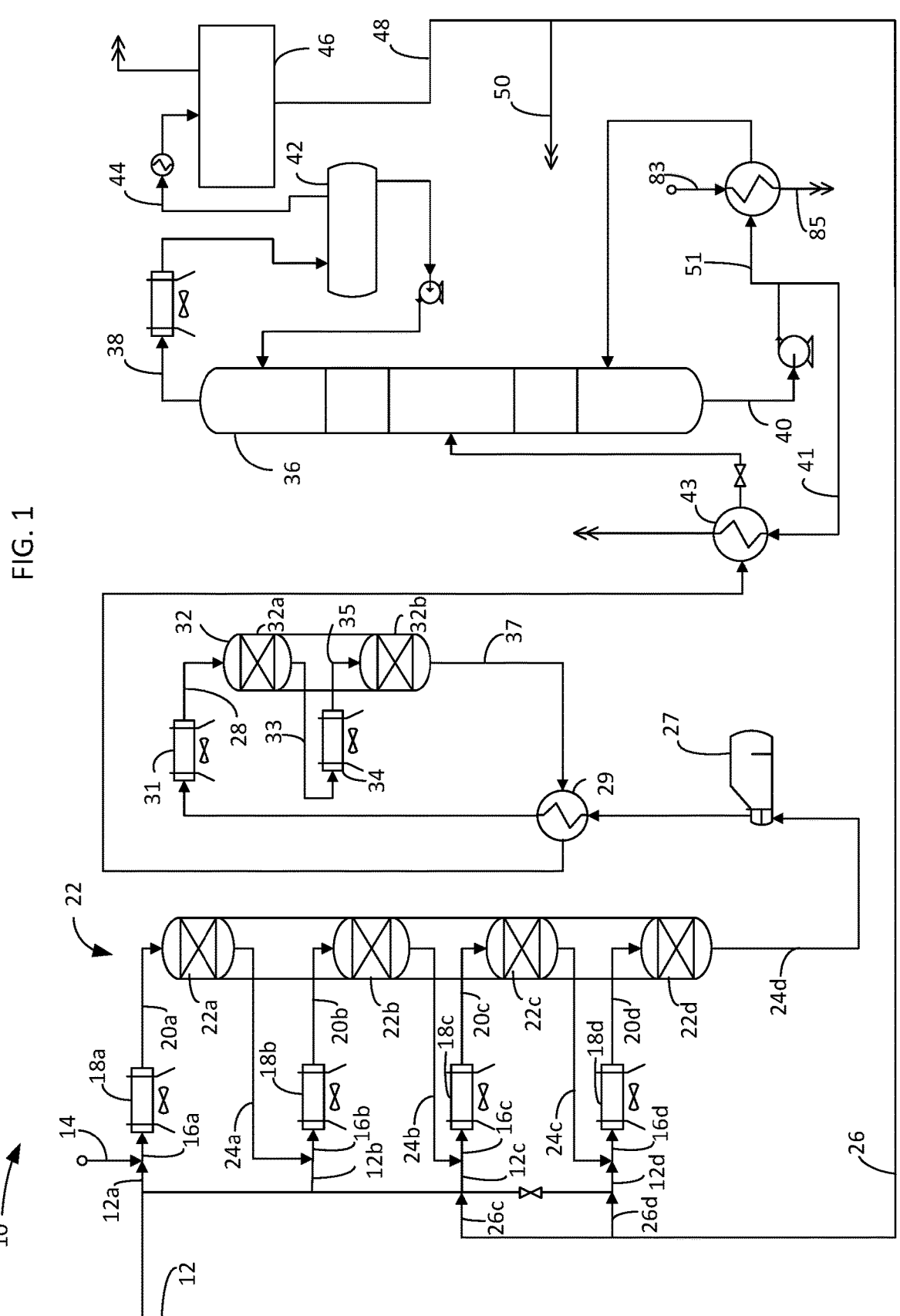
FIG. 1 is a schematic drawing of an oligomerization section of a process and apparatus of the present disclosure.

The term "communication" means that fluid flow is operatively permitted between enumerated components, which may be characterized as "fluid communication".

The term "downstream communication" means that at least a portion of fluid flowing to the subject in downstream communication may operatively flow from the object with which it fluidly communicates.

The term "upstream communication" means that at least a portion of the fluid flowing from the subject in upstream communication may operatively flow to the object with which it fluidly communicates.

The term "direct communication" means that fluid flow from the upstream component enters the downstream component without passing through any other intervening vessel.

The term "indirect communication" means that fluid flow from the upstream component enters the downstream component after passing through an intervening vessel.

The term "bypass" means that the object is out of downstream communication with a bypassing subject at least to the extent of bypassing.

As used herein, the term "predominant" or "predominate" means greater than 50%, suitably greater than 75% and preferably greater than 90%.

The term "column" means a distillation column or columns for separating one or more components of different volatilities. Unless otherwise indicated, each column includes a condenser on an overhead of the column to condense and reflux a portion of an overhead stream back to the top of the column and a reboiler at a bottom of the column to vaporize and send a portion of a bottoms stream back to the bottom of the column. Feeds to the columns may be preheated. The top pressure is the pressure of the overhead vapor at the vapor outlet of the column. The bottom temperature is the liquid bottom outlet temperature. Overhead lines and bottoms lines refer to the net lines from the column downstream of any reflux or reboil to the column. Stripper columns may omit a reboiler at a bottom of the column and instead provide heating requirements and separation impetus from a fluidized inert media such as steam. Stripping columns typically feed a top tray and take main product from the bottom.

As used herein, the term "separator" means a vessel which has an inlet and at least an overhead vapor outlet and a bottoms liquid outlet and may also have an aqueous stream outlet from a boot. A flash drum is a type of separator which may be in downstream communication with a separator that may be operated at higher pressure. As used herein, the term "boiling point temperature" means atmospheric equivalent boiling point (AEBP) as calculated from the observed boiling temperature and the distillation pressure, as calculated using the equations furnished in ASTM D1160 appendix A7 entitled "Practice for Converting Observed Vapor Temperatures to Atmospheric Equivalent Temperatures".

As used herein, the term "True Boiling Point" (TBP) means a test method for determining the boiling point of a material which corresponds to ASTM D-2892 for the production of a liquefied gas, distillate fractions, and residuum of standardized quality on which analytical data can be obtained, and the determination of yields of the above fractions by both mass and volume from which a graph of temperature versus mass % distilled is produced using fifteen theoretical plates in a column with a 5:1 reflux ratio.

As used herein, the term "T5", "T90" or "T95" means the temperature at which 5 mass percent, 90 mass percent or 95 mass percent, as the case may be, respectively, of the sample boils using ASTM D-86 or TBP.

As used herein, the term "initial boiling point" (IBP) means the temperature at which the sample begins to boil using ASTM D-7169, ASTM D-86 or TBP, as the case may be.

As used herein, the term "end point" (EP) means the temperature at which the sample has all boiled off using ASTM D-7169, ASTM D-86 or TBP, as the case may be.

As used herein, the term "diesel" means hydrocarbons boiling in the range of an IBP between about 125° C. (257° F.) and about 175° C. (347° F.) or a T5 between about 150° C. (302° F.) and about 200° C. (392° F.) and the "diesel cut point" comprising a T95 between about 343° C. (650° F.) and about 399° C. (750° F.) using the TBP distillation method or a T90 between 280° C. (536° F.) and about 340° C. (644° F.) using ASTM D-86. The term "green diesel" means diesel comprising hydrocarbons not sourced from fossil fuels.

As used herein, the term "jet fuel" means hydrocarbons boiling in the range of a T10 between about 190° C. (374° F.) and about 215° C. (419° F.) and an end point of between about 290° C. (554° F.) and about 310° C. (590° F.). The term "green jet fuel" means jet fuel comprising hydrocarbons not sourced from fossil fuels.

DETAILED DESCRIPTION

The process disclosed involves oligomerizing an olefin stream comprising ethylene in a first oligomerization stage followed by further oligomerizing the ethylene oligomers in a second oligomerization stage. The process utilizes a zeolitic catalyst for first stage oligomerization of ethylene and a metal catalyst for second stage oligomerization.

Figure 2:
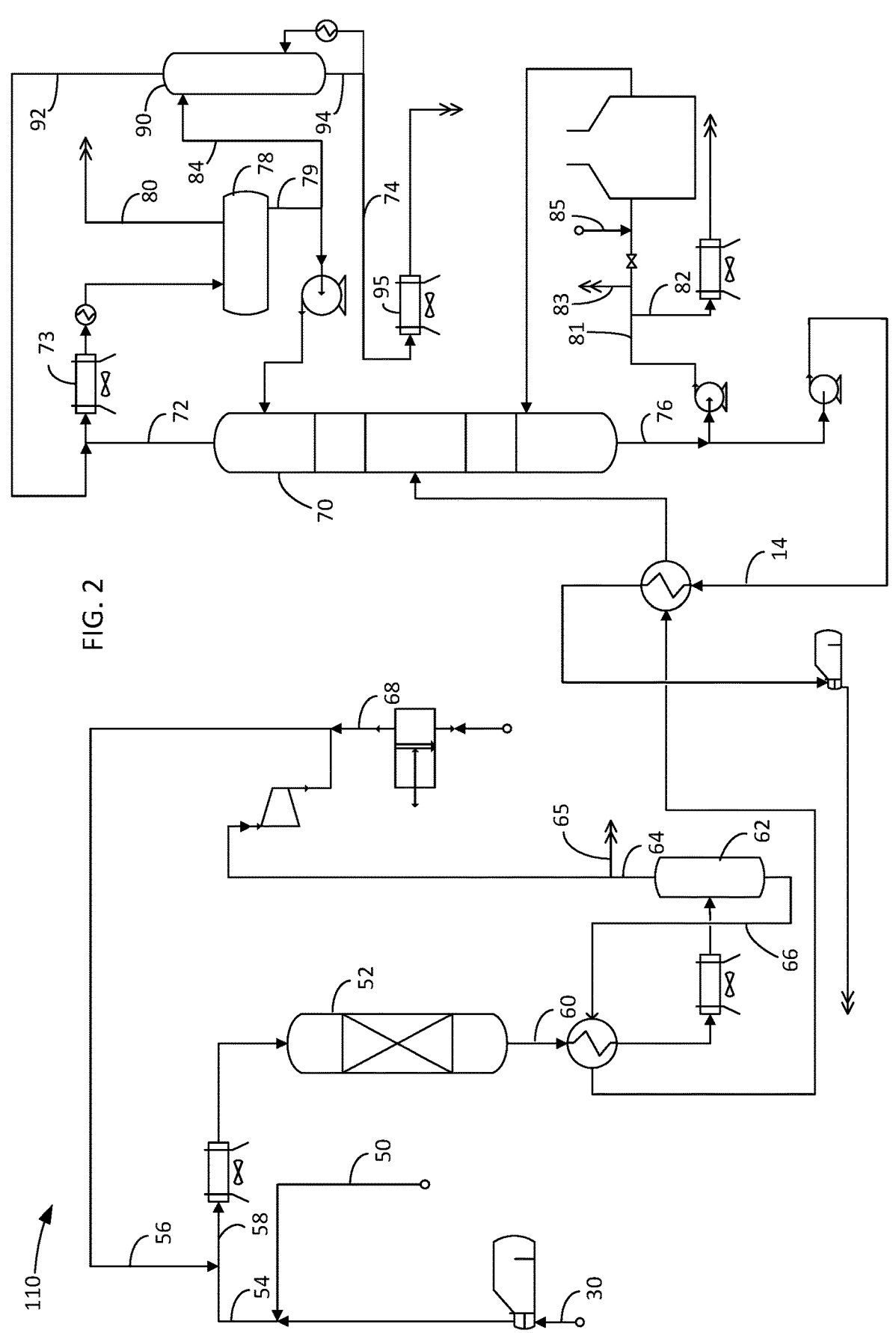
FIG. 2 is a schematic drawing of a hydrogenation section of a process and apparatus of the present disclosure.

The process and apparatus may include an oligomerization section 10 in FIG. 1 and a hydrogenation section 110 in FIG. 2.

Turning to the oligomerization section 10 of FIG. 1, a charge olefin stream in line 12 is provided to the oligomerization section 10. The charge olefin stream may comprise substantial ethylene. The charge olefin stream may predominantly comprise ethylene. In an aspect, the charge olefin stream may comprise at least 95 mol % ethylene. The charge olefin stream in line 12 may be styled an ethylene stream. The olefin stream may be provided by the dehydration of ethanol or provided from a MTO unit. The charge olefin stream may be at a temperature of about 60° C. (140° F.) to about 150° C. (302° F.), preferably about 80° C. (176° F.) to about 100° C. (212° F.) and a pressure of about 3.5 MPag (500 psig) to about 8.4 MPag (1200 psig).

The olefin stream may be initially contacted with a first stage oligomerization catalyst to oligomerize the ethylene to dimers and oligomers and then contacted with a second stage oligomerization catalyst to oligomerize oligomerized ethylene. The dimerization reaction generates a large exotherm. For example, dimerization of ethylene can generate 612 kcal/kg (1100 BTU/lb) of heat. Consequently, this large exotherm must be managed.

Accordingly, the olefin stream in line 12 may be split into multiple olefin streams. In FIG. 1, the olefin stream is split into four separate streams: a first olefin stream in charge line 12a, a second olefin stream in charge line 12b, a third olefin stream in charge line 12c and a fourth or last olefin stream in charge line 12d. In an embodiment, no flow may be permitted through the control valve in charge line 12d, so the charge olefin stream is only fed to the upstream catalyst beds 22a-22c. More or less separate multiple olefin streams may be used. Up to six olefin streams are readily contemplated. The charge olefin stream in line 12 may be split into equal aliquot multiple olefin streams. Alternatively, the charge olefin stream in line 12 may be split into unequal streams. For example, the charge olefin stream may be split into streams of ascending flow rates in which a subsequent olefin stream has a larger flow rate than a preceding stream. In an embodiment, the charge olefin stream is split into three streams of a predominance of the flow rate of the charge olefin stream from line 12 such as about 40 to about 60% in line 12a and less than a predominance of the flow rate of the charge olefin stream from line 12 in lines 12b and 12c, such as about 15 to about 40%, and no flow in line 12d. Preferably, the flow rate of the charge olefin stream fed to the upstream bed 22a is the highest of the upstream catalyst beds 22a to 22c.

To manage the exotherm, the olefin stream may be diluted with a diluent stream to provide a diluted olefin stream to absorb the exotherm. The diluent stream may comprise a paraffin stream in a diluent line 14. The diluent stream in the diluent line 14 may be added to the charge olefin stream in line 12 before the charge olefin stream is split into multiple olefin streams. Preferably, the diluent stream is added to the first olefin stream in line 12a after the split into multiple olefin streams to provide a first diluted olefin stream in line 16a, so the diluent stream passes through all of first stage oligomerization reactions. Alternatively, the diluent stream may also be split into multiple parallel streams with each diluent stream added to a corresponding olefin stream. The diluent stream may have a volumetric flow rate of about 2 to about 8 times and preferably about 3 to about 6 times the mass flow rate of the charge olefin stream in line 12. The first diluted olefin stream may comprise no more than 35 wt % olefins, suitably no more than 17 wt % olefins and preferably no more than 6 wt % olefins. The first diluted olefin stream may comprise no more than 35 wt % ethylene, suitably no more than 14 wt % ethylene and preferably no more than 6 wt % ethylene. The first diluted olefin stream may comprise no more than 35 wt % propylene, suitably no more than 14 wt % propylene and preferably no more than 6 wt % propylene.

The first diluted olefin stream in line 16a may be cooled in a first charge cooler 18a to provide a first cooled diluted olefin stream in line 20a and charged to a first bed 22a of first stage oligomerization catalyst in a first stage oligomerization reactor 22. The cooled diluted first charge olefin stream in line 20a may be charged at a temperature of about 180° C. (356° F.) to about 260° C. (500° F.) and a pressure of about 3.5 MPag (500 psig) to about 8.4 MPag (1200 psig). The charge cooler 18a may comprise a steam generator. The first stage oligomerization reactor 22 may comprise a series of first stage oligomerization catalyst beds 22a, 22b, 22c and 22d for charging each with multiple olefin streams 12a, 12b, 12c, and 12d, respectively. As earlier stated, in an embodiment, no charge olefin stream may be in line 12d, so in this embodiment the charge olefin stream from line 12 is only fed to the upstream first stage oligomerization catalyst beds 22a-22c. The first stage oligomerization reactor preferably contains four fixed first stage oligomerization catalyst beds 22a, 22b, 22c and 22d. It is also contemplated that each first stage oligomerization catalyst bed 22a, 22b, 22c and 22d may be in a dedicated first stage oligomerization reactor or multiple first stage oligomerization catalyst beds may be in two or more separate first stage oligomerization reactors. Up to six first stage oligomerization catalyst beds are readily contemplated. A parallel first stage oligomerization reactor may be used when the first stage oligomerization reactor 22 has deactivated during which the first stage oligomerization reactor 22 is regenerated in situ by combustion of coke from the catalyst.

A recycle olefin stream in line 26 may be charged to the first stage oligomerization catalyst beds 22a-22d. In an embodiment, the recycle olefin stream is only fed to the downstream catalyst beds 22c and 22d. The recycle olefin stream in line 26 may be split into multiple recycle olefin streams in lines 26c and 26d and fed to first stage oligomerization catalyst beds 22c and 22d, respectively. In an embodiment, line 26c may have a predominance of the flow rate and 26d may have the remainder of flow rate of the recycle olefin stream in line 26. Preferably, more of the flow rate of the recycle olefin stream is fed to the upstream bed 22*c* of the downstream catalyst beds 22*c* and 22*d*. In an embodiment, the first stage catalyst bed 22*c* is an upstream bed for purposes of the charge olefin from line 12 and a downstream bed for purposes of the recycle olefin feed from line 26.

The first cooled, diluted olefin stream may be charged to the first catalyst bed 22*a* in line 20*a* preferably in a down flow operation. However, upflow operation may be suitable. As first stage oligomerization of ethylene occurs in the first stage oligomerization catalyst bed 22*a*, an exotherm is generated due to the exothermic nature of the ethylene first stage oligomerization reaction. First stage oligomerization of the first olefin stream produces a first oligomerized olefin stream in a first oligomerized effluent line 24*a* at an elevated outlet temperature despite the cooling and dilution. The elevated outlet temperature is limited to between 25° C. (45° F.) and about 61° C. (110° F.) above the inlet temperature to the catalyst bed 22*a*.

The second olefin stream in line 12*b* may be diluted with the first oligomerized olefin stream in line 24*a* removed from the first, first stage oligomerization catalyst bed 22*a* to provide a second diluted olefin stream in line 16*b*. The first oligomerized olefin stream in line 24*a* includes the diluent stream from diluent line 14 added to the first olefin stream in line 12*a*. The second diluted olefin stream may comprise no more than 35 wt % olefins, suitably no more than 22 wt % olefins and preferably no more than 15 wt % olefins. The second diluted olefin stream may comprise no more than 35 wt % ethylene, suitably no more than 15 wt % ethylene and preferably no more than 6 wt % ethylene. The second diluted olefin stream may comprise no more than 35 wt % propylene, suitably no more than 15 wt % propylene and preferably no more than 6 wt % propylene. The second diluted olefin stream in line 16*b* may be cooled in a second charge cooler 18*b* which may be located externally to the first stage oligomerization reactor 22 to provide a second cooled diluted olefin stream in line 20*b* and charged to a second bed 22*b* of first stage oligomerization catalyst in a first stage oligomerization reactor 22. The second charge cooler 18*b* may be steam generator. The second cooled diluted olefin stream in line 20*b* may be charged at a temperature of about 180° C. (356° F.) to about 260° C. (500° F.) and a pressure of about 3.5 MPag (500 psig) to about 8.4 MPag (1200 psig). The second diluted olefin stream will include diluent and olefins from the first oligomerized olefin stream. The olefins from the first oligomerized olefin stream will further oligomerize in the second catalyst bed 22*b*. First stage oligomerization of ethylene in the second olefin stream in the second bed 22*b* of first stage oligomerization catalyst produces a second oligomerized olefin stream in a second oligomerized effluent line 24*b* at an elevated outlet temperature. The elevated outlet temperature may be limited to between 25° C. (45° F.) and about 61° C. (110° F.) above the inlet temperature to the second, first stage catalyst bed 22*b*.

The third olefin stream in line 12*c* may be diluted with the second oligomerized olefin stream in line 24*b* removed from the first stage oligomerization reactor 22 and mixed with a first recycle olefin stream in line 26*c* to provide a third diluted olefin stream in line 16*c*. The second oligomerized olefin stream in line 24*b* includes the diluent stream from diluent line 14 added to the first olefin stream in line 12*a*. The third diluted olefin stream may comprise no more than 35 wt % olefins, suitably no more than 23 wt % olefins and preferably no more than 15 wt % olefins. The third diluted olefin stream may comprise no more than 35 wt % ethylene, suitably no more than 13 wt % ethylene and preferably no more than 6 wt % ethylene. The third diluted olefin stream may comprise no more than 35 wt % propylene, suitably no more than 13 wt % propylene and preferably no more than 6 wt % propylene. The third diluted olefin stream in line 16*c* may be cooled in a third charge cooler 18*c* which may be located externally to the first stage oligomerization reactor 22 to provide a third cooled diluted olefin stream in line 20*c* and charged to a third bed 22*c* of first stage oligomerization catalyst in the first stage oligomerization reactor 22. The third charge cooler 18*c* may be a steam generator. The third cooled diluted olefin stream in line 20*c* may be charged at a temperature of about 180° C. (356° F.) to about 260° C. (500° F.) and a pressure of about 3.5 MPag (500 psig) to about 8.4 MPag (1200 psig). The third diluted olefin stream will include diluent and olefins from the second oligomerized olefin stream and from the first recycle olefin stream. The olefins from the second oligomerized olefin stream and the first recycle olefin stream will further oligomerize in the third, first stage oligomerization catalyst bed 22*c*. Oligomerization of ethylene in the third diluted olefin stream in the third bed 22*c* of first stage oligomerization catalyst produces a third oligomerized olefin stream in a third oligomerized effluent line 24*c* at an elevated outlet temperature. In an embodiment, the third oligomerized olefin stream is a penultimate oligomerized olefin stream and the third oligomerized effluent line 24*c* is a penultimate oligomerized effluent line 24*c*. The elevated outlet temperature is limited to between 25° C. (45° F.) and about 61° C. (110° F.) above the inlet temperature to the catalyst bed 22*c*.

The fourth olefin stream in line 12*d* may be diluted with the third or penultimate oligomerized olefin stream in line 24*c* removed from the third, first stage oligomerization catalyst bed 22*c* of the first stage oligomerization reactor 22 and the second recycle olefin stream in line 26*d* to provide a fourth diluted olefin stream in line 16*d*. The third or penultimate oligomerized olefin stream in line 24*c* includes the diluent stream from diluent line 14 added to the first olefin stream in line 12*a*. The fourth diluted olefin stream may comprise no more than 35 wt % olefins, suitably no more than 24 wt % olefins and preferably no more than 15 wt % olefins. The fourth diluted olefin stream may comprise no more than 35 wt % ethylene, suitably no more than 11 wt % ethylene and preferably no more than 6 wt % ethylene. The fourth diluted olefin stream may comprise no more than 35 wt % propylene, suitably no more than 11 wt % propylene and preferably no more than 6 wt % propylene. The fourth diluted olefin stream in line 16*d* may be cooled in a fourth charge cooler 18*d* which may be located externally to the first stage oligomerization reactor 22 to provide a fourth cooled diluted olefin stream in line 20*d* and charged to a fourth bed 22*d* of first stage oligomerization catalyst in the first stage oligomerization reactor 22. The fourth charge cooler 18*d* may be a steam generator. The fourth cooled diluted olefin stream in line 20*d* may be charged at a temperature of about 180° C. (356° F.) to about 260° C. (500° F.) and a pressure of about 3.5 MPag (500 psig) to about 8.4 MPag (1200 psig). The fourth or last diluted olefin stream will include diluent and olefins from the third or penultimate oligomerized olefin stream and the second recycle olefin stream. The olefins from the third or penultimate oligomerized olefin stream and the second recycle olefin stream will oligomerize in the fourth catalyst bed 22*d*. Oligomerization of ethylene and oligomers in the fourth olefin stream in the fourth, first stage catalyst bed 22*d* of first stage oligomerization catalyst produces a fourth oligomerized olefin stream in a fourth oligomerized effluent line 24*d* at an elevated outlet temperature. The elevated outlet temperature is limited to between 25° C. (45° F.) and about 61° C. (110° F.) above the inlet temperature to the fourth, first stage catalyst bed 22*d*.

The recycle olefin stream 26*c* and 26*d* provide olefins that can dimerize over the catalyst beds 22*c* and 22*d*, respectively, but can also help manage the exotherm generated during oligomerization of ethylene and olefins.

In an embodiment, the fourth olefin stream in line 12*d* is a last olefin stream, the fourth oligomerized olefin stream is a last oligomerized olefin stream and the fourth oligomerized effluent line 24*d* is a last oligomerized effluent line 24*d*.

The first stage oligomerization reaction takes place predominantly in the liquid phase or in a mixed liquid and gas phase at a LHSV 0.5 to 10 $hr^{-1}$ on an olefin basis. We have found that a predominant fraction of ethylene in the olefin stream converts to higher olefins. Typically, at least 30 to about 50 mol % of ethylene will dimerize and oligomerize across a first stage oligomerization catalyst bed. The ethylene will initially dimerize over the catalyst to butenes.

The first stage oligomerization catalyst may include a zeolitic catalyst. The first stage oligomerization catalyst may be considered a solid acid catalyst. The zeolite may comprise between about 5 and about 95 wt % of the catalyst, for example between about 5 and about 85 wt %. Suitable zeolites include zeolites having a structure from one of the following classes: MFI, MEL, ITH, IMF, TUN, FER, BEA, FAU, BPH, MEI, MSE, MWW, UZM-8, MOR, OFF, MTW, TON, MTT, AFO, ATO, and AEL. 3-letter codes indicating a zeotype are as defined by the Structure Commission of the International Zeolite Association and are maintained at http://www.iza-structure.org/databases. UZM-8 is as described in U.S. Pat. No. 6,756,030. In a preferred aspect, the first stage oligomerization catalyst may comprise a zeolite with a framework having a ten-ring pore structure. Examples of suitable zeolites having a ten-ring pore structure include TON, MTT, MFI, MEL, AFO, AEL, EUO and FER. In a further preferred aspect, the first stage oligomerization catalyst comprising a zeolite having a ten-ring pore structure may comprise a uni-dimensional pore structure. A uni-dimensional pore structure indicates zeolites containing non-intersecting pores that are substantially parallel to one of the axes of the crystal. The pores preferably extend through the zeolite crystal. Suitable examples of zeolites having a ten-ring uni-dimensional pore structure may include MTT. In a further aspect, the first stage oligomerization catalyst comprises an MTT zeolite.

The first stage oligomerization catalyst may be formed by combining the zeolite with a binder, and then forming the catalyst into pellets. The pellets may optionally be treated with a phosphorus reagent to create a zeolite having a phosphorous component between 0.5 and 15 wt % of the treated catalyst. The binder is used to confer hardness and strength on the catalyst. Binders include alumina, aluminum phosphate, silica, silica-alumina, zirconia, titania and combinations of these metal oxides, and other refractory oxides, and clays such as montmorillonite, kaolin, palygorskite, smectite and attapulgite. A preferred binder is an aluminum-based binder, such as alumina, aluminum phosphate, silica-alumina and clays.

One of the components of the catalyst binder utilized in the present invention is alumina. The alumina source may be any of the various hydrous aluminum oxides or alumina gels such as alpha-alumina monohydrate of the boehmite or pseudo-boehmite structure, alpha-alumina trihydrate of the gibbsite structure, beta-alumina trihydrate of the bayerite structure, and the like. A suitable alumina is available from UOP LLC under the trademark VERSAL. A preferred alumina is available from Sasol North America Alumina Product Group under the trademark Catapal. This material is an extremely high purity alpha-alumina monohydrate (pseudo-boehmite) which after calcination at a high temperature has been shown to yield a high purity gamma-alumina.

A suitable first stage oligomerization catalyst is prepared by mixing proportionate volumes of zeolite and alumina to achieve the desired zeolite-to-alumina ratio. In an embodiment, the MTT content may about 5 to 85, for example about 20 to 82 wt % MTT zeolite, and the balance alumina powder will provide a suitably supported catalyst. A silica support is also contemplated.

Monoprotic acid such as nitric acid or formic acid may be added to the mixture in aqueous solution to peptize the alumina in the binder. Additional water may be added to the mixture to provide sufficient wetness to constitute a dough with sufficient consistency to be extruded or spray dried. Extrusion aids such as cellulose ether powders can also be added. A preferred extrusion aid is available from The Dow Chemical Company under the trademark Methocel.

The paste or dough may be prepared in the form of shaped particulates, with the preferred method being to extrude the dough through a die having openings therein of desired size and shape, after which the extruded matter is broken into extrudates of desired length and dried. A further step of calcination may be employed to give added strength to the extrudate. Generally, calcination is conducted in a stream of air at a temperature from about 260° C. (500° F.) to about 815° C. (1500° F.). The MTT catalyst is not selectivated to neutralize acid sites such as with an amine.

The extruded particles may have any suitable cross-sectional shape, i.e., symmetrical or asymmetrical, but most often have a symmetrical cross-sectional shape, preferably a spherical, cylindrical or polylobal shape. The cross-sectional diameter of the particles may be as small as m; however, it is usually about 0.635 mm (0.25 inch) to about 12.7 mm (0.5 inch), preferably about 0.79 mm (1/32 inch) to about 6.35 mm (0.25 inch), and most preferably about 0.06 mm (1/24 inch) to about 4.23 mm (1/6 inch).

In one exemplary embodiment, an MTT-type zeolite catalyst disposed on a high purity pseudo boehmite alumina substrate in a ratio of about 90/10 to about 20/80 and preferably between about 20/80 and about 50/50 is provided in a catalyst bed or more in the first stage oligomerization reactor 22.

The first stage oligomerization catalyst can be regenerated upon deactivation. Suitable regeneration conditions include subjecting the first stage oligomerization catalyst, for example, in situ, to hot air at 500° C. for 3 hours. In practice, regeneration may be effected by hot nitrogen purge at about 300 to about 500° C., suitably about 350 to about 450° C. to strip heavy hydrocarbon species from the spent catalyst. Alternatively, the spent catalyst may be purged with a stream of light olefins, may be washed with a solvent, or with another hydrocarbon stream. The purge or wash step is followed by coke burn in about 0.3 to about 0.7 mol % oxygen for 20 to 40 hours and a proof burn in about 3 to about 10 mol % oxygen until most of the coke is burned to no more than 1.2 wt % coke on catalyst. To facilitate regeneration without downtime, a swing bed arrangement may be employed with an alternative first stage oligomerization reactor. Alternatively, a lead-lag swing bed arrangement may be employed. A regeneration gas stream may be admitted to the first stage oligomerization reactor 22 requiring regeneration. The regeneration gas may comprise air with an increased or decreased concentration of oxygen. Activity and selectivity of the regenerated catalyst is comparable to fresh catalyst.

The zeolite catalyst is advantageous as a first stage oligomerization catalyst. The zeolitic catalyst has relatively low sensitivity towards oxygenates contamination. Consequently, less removal of oxygenates is required of olefinic feed in line 12 if produced from an ethanol dehydration process.

The last oligomerized olefin stream in the last oligomerized effluent line 24d has an increased concentration of ethylene dimers and oligomers compared to the charge olefin stream in line 12. The oligomerized olefin stream is cooled to generate steam in a steam generator 27, then cooled by heat exchange with an oligomerate stream in line 37 in a heat exchanger 29 and then cooled in an air cooler 31 before it is charged to a second stage oligomerization reactor 32 in an oligomerization charge line 28. The oligomerization reactor 32 may comprise a series of oligomerization catalyst beds 32a and 32b assembled in series. It is also contemplated that each second stage oligomerization catalyst bed 32a and 32b may be in a dedicated oligomerization reactor or multiple oligomerization catalyst beds may be in two or more separate oligomerization reactors. More than two second stage oligomerization catalyst beds are readily contemplated. A parallel second stage oligomerization reactor may be used when the second stage oligomerization reactor 32 has deactivated during which the second stage oligomerization reactor 32 is regenerated in situ by combustion of coke from the catalyst.

To achieve the most desirable olefin product, the second stage oligomerization reactor 32 may be operated at a temperature from about 38° C. (100° F.) to about 180° C. (356° F.). The second stage oligomerization reactor 32 may be run at a pressure of about 4.9 MPa (700 psig) to about 7.6 MPa (1100 psig), and more preferably from about 3.4 MPa (500 psig) to about 8.3 MPa (1200 psig). A first oligomerate stream from a first, second stage oligomerization catalyst bed 32a may be withdrawn from the second stage oligomerization reactor 32 in line 33a, cooled in a cooler 34 back to a temperature of about 38° C. (100° F.) to about 180° C. (356° F.) and charged to the second, second stage oligomerization catalyst bed 32b in line 35.

The second stage oligomerization reactor 32 may be in downstream communication with the first stage oligomerization reactor 22. The second stage oligomerization reactor 32 preferably operates in a down flow operation. However, upflow operation may be suitable. The charge oligomerized olefin stream in the second stage charge line 28 is contacted with the second stage oligomerization catalyst to dimerize, trimerize and tetramerize unconverted ethylene. With regard to the second stage oligomerization reactor 32, process conditions may be selected to produce a higher percentage of jet range olefins which, when hydrogenated in a subsequent step as will be described below, result in a desirable jet-range hydrocarbon product. A predominance of the unconverted ethylene in the charge oligomerized olefin stream is oligomerized. In an embodiment, at least 99 mol % of butenes in the charge oligomerized olefin stream are oligomerized. The metal oligomerization catalyst is efficient at dimerizing and oligomerizing un-oligomerized ethylene from the first stage oligomerization. An oligomerate stream with an increased average carbon number greater than the oligomerized olefin stream charged in the oligomerization charge line 28 exits the oligomerization reactor 32 in line 37.

The second stage oligomerization catalyst may comprise a metal catalyst and preferably a metal on a support. The second stage oligomerization catalyst is preferably an amorphous silica-alumina base with a metal from either Group VIII and/or Group VIB in the periodic table using Chemical Abstracts Service notations. In an aspect, the catalyst has a Group VIII metal promoted with a Group VIB metal. Typically, the silica and alumina will only be in the base, so the silica-to-alumina ratio will be the same for the catalyst as for the base. The metals can either be impregnated onto or ion exchanged with the silica-alumina base. Co-mulling is also contemplated. Catalysts for the present invention may have a Low Temperature Acidity Ratio of at least about 0.15, suitably of about 0.2, and preferably greater than about 0.25, as determined by Ammonia Temperature Programmed Desorption (Ammonia TPD) as described hereinafter. Additionally, a suitable catalyst will have a surface area of between about 50 and about 400 m²/g as determined by nitrogen BET.

The preferred second stage oligomerization catalyst comprises an amorphous silica-alumina support. One of the components of the catalyst support utilized in the present invention is alumina. The alumina may be any of the various hydrous aluminum oxides or alumina gels such as alpha-alumina monohydrate of the boehmite or pseudo-boehmite structure, alpha-alumina trihydrate of the gibbsite structure, beta-alumina trihydrate of the bayerite structure, and the like. A particularly preferred alumina is available from Sasol North America Alumina Product Group under the trademark Catapal. This material is an extremely high purity alpha-alumina monohydrate (pseudo-boehmite) which after calcination at a high temperature has been shown to yield a high purity gamma-alumina. Another component of the catalyst support is an amorphous silica-alumina. A suitable silica-alumina with a silica-to-alumina ratio of 2.6 is available from CCIC, a subsidiary of JGC, Japan.

Another component utilized in the preparation of the second stage oligomerization catalyst utilized in the present invention is a surfactant. The surfactant is preferably admixed with the hereinabove described alumina and the silica-alumina powders. The resulting admixture of surfactant, alumina and silica-alumina is then formed, dried and calcined as hereinafter described. The calcination effectively removes by combustion the organic components of the surfactant but only after the surfactant has dutifully performed its function in accordance with the present invention. Any suitable surfactant may be utilized in accordance with the present invention. A preferred surfactant is a surfactant selected from a series of commercial surfactants sold under the trademark "Antarox" by Solvay S. A. The "Antarox" surfactants are generally characterized as modified linear aliphatic polyethers and are low-foaming biodegradable detergents and wetting agents.

A suitable silica-alumina mixture is prepared by mixing proportionate volumes silica-alumina and alumina to achieve the desired silica-to-alumina ratio. In an embodiment, about 75 to about 95 wt-% amorphous silica-alumina with a silica-to-alumina ratio of 2.6 and about 10 to about 20 wt-% alumina powder will provide a suitable support. In an embodiment, other ratios of amorphous silica-alumina to alumina may be suitable.

Any convenient method may be used to incorporate a surfactant with the silica-alumina and alumina mixture. The surfactant is preferably admixed during the admixture and formation of the alumina and silica-alumina. A preferred method is to admix an aqueous solution of the surfactant with the blend of alumina and silica-alumina before the final formation of the support. It is preferred that the surfactant be present in the paste or dough in an amount from about 0.01 to about 10 wt-% based on the weight of the alumina and silica-alumina.

Monoprotic acid such as nitric acid or formic acid may be added to the mixture in aqueous solution to peptize the alumina in the binder. Additional water may be added to the mixture to provide sufficient wetness to constitute a dough with sufficient consistency to be extruded or spray dried.

The paste or dough may be prepared in the form of shaped particulates, with the preferred method being to extrude the dough mixture of alumina, silica-alumina, surfactant and water through a die having openings therein of desired size and shape, after which the extruded matter is broken into extrudates of desired length and dried. A further step of calcination may be employed to give added strength to the extrudate. Generally, calcination is conducted in a stream of dry air at a temperature from about 260° C. (500° F.) to about 815° C. (1500° F.).

The extruded particles may have any suitable cross-sectional shape, i.e., symmetrical or asymmetrical, but most often have a symmetrical cross-sectional shape, preferably a spherical, cylindrical or polylobal shape. The cross-sectional diameter of the particles may be as small as m; however, it is usually about 0.635 mm (0.25 inch) to about 12.7 mm (0.5 inch), preferably about 0.79 mm (1/32 inch) to about 6.35 mm (0.25 inch), and most preferably about 0.06 mm (1/24 inch) to about 4.23 mm (1/6 inch).

Typical characteristics of the amorphous silica-alumina supports utilized herein are a total pore volume, average pore diameter and surface area large enough to provide substantial space and area to deposit the active metal components. The total pore volume of the support, as measured by conventional mercury porosimeter methods, is usually about 0.2 to about 2.0 cc/gram, preferably about 0.25 to about 1.0 cc/gram and most preferably about 0.3 to about 0.9 cc/gram. Ordinarily, the amount of pore volume of the support in pores of diameter greater than 100 angstroms is less than about 0.1 cc/gram, preferably less than 0.08 cc/gram, and most preferably less than about 0.05 cc/gram. Surface area, as measured by the B.E.T. method, is typically above 50 m²/gram, e.g., above about 200 m²/gram, preferably at least 250 m²/gram, and most preferably about 300 m² gram to about 400 m²/gram.

To prepare the second stage oligomerization catalyst, the support material is compounded, as by a single impregnation or multiple impregnations of a calcined amorphous refractory oxide support particles, with one or more precursors of at least one metal component from Group VIII or VIB of the periodic table. The Group VIII metal, preferably nickel, should be present in a concentration of about 0.5 to about 15 wt-% and the Group VIB metal, preferably tungsten, should be present in a concentration of about 0 to about 12 wt-%. The impregnation may be accomplished by any method known in the art, as for example, by spray impregnation wherein a solution containing the metal precursors in dissolved form is sprayed onto the support particles. Another method is the multi-dip procedure wherein the support material is repeatedly contacted with the impregnating solution with or without intermittent drying. Yet other methods involve soaking the support in a large volume of the impregnation solution or circulating the support therein, and yet one more method is the pore volume or pore saturation technique wherein support particles are introduced into an impregnation solution of volume just sufficient to fill the pores of the support. On occasion, the pore saturation technique may be modified, so as to utilize an impregnation solution having a volume between 10 percent less and 10 percent more than that which will just fill the pores.

If the active metal precursors are incorporated by impregnation, a subsequent or second calcination at elevated temperatures, as for example, between 399° C. (750° F.) and 760° C. (1400° F.), converts the metals to their respective oxide forms. In some cases, calcinations may follow each impregnation of individual active metals. A subsequent calcination yields a catalyst containing the active metals in their respective oxide forms.

A preferred second stage oligomerization catalyst of the present invention has an amorphous silica-alumina base impregnated with 0.5-15 wt-% nickel in the form of 3.175 mm (0.125 inch) extrudates and a density of about 0.45 to about 0.65 g/ml. It is also contemplated that metals can be incorporated onto the support by other methods such as ion-exchange and co-mulling.

The second stage oligomerization catalyst can be regenerated upon deactivation. Suitable regeneration conditions include subjecting the catalyst, for example, in situ, to hot air at 500° C. for 3 hours. In practice, regeneration may be effected by hot nitrogen purge at about 300 to about 500° C., suitably about 350 to about 450° C. to strip heavy hydrocarbon species from the spent catalyst. Alternatively, the spent catalyst may be purged with a stream of light olefins, may be washed with a solvent, or with another hydrocarbon stream. The purge or wash step is followed by coke burn in about 0.3 to about 0.7 mol % oxygen for 20 to 40 hours and a proof burn in about 3 to about 10 mol % oxygen until all coke is burned. To facilitate regeneration without downtime, a swing bed arrangement may be employed with an alternative second stage oligomerization reactor. The regeneration gas may comprise air with an increased or decreased concentration of oxygen. Activity and selectivity of the regenerated catalyst is comparable to fresh catalyst.

Oligomerization reactions are also exothermic in nature. The last oligomerized olefin stream in line 24d includes the diluent stream from diluent line 14 added to the first olefin stream in line 12a and carried through the first stage oligomerization catalyst beds 22a-22d. The diluent stream is then transported into the second stage oligomerization reactor 32 in line 28 to absorb the exotherm in the second stage oligomerization reactor.

When the oligomerization reaction is performed according to the above-noted process conditions, a C4 olefin conversion of greater than or equal to about 95% is achieved, or greater than or equal to 97%. The resulting oligomerate stream in line 37 includes a plurality of olefin products that are distillate range hydrocarbons.

An oligomerate stream in line 37 with an increased C9+ olefin concentration compared to the charge oligomerized olefin stream in line 28 is heat exchanged with the last oligomerized stream in line 24d in the heat exchanger 29 and an olefin splitter bottoms stream in line 41 in a heat exchanger 43, let down in pressure and fed to an olefin splitter column 36. The oligomerate stream in line 37 may be at a temperature from about 140° C. (284° F.) to about 200° C. (392° F.) and a pressure of about 3.4 MPa (gauge) (500 psig) to about 8.3 MPa (gauge) (1200 psig) and preferably about 3.9 MPa (gauge) (550 psig) to about 6.3 MPa (gauge) (900 psig).

In the olefin splitter column 36 oligomers that boil lower than the jet range hydrocarbons, typically C8-hydrocarbons with atmospheric boiling points less than about 150° C., are separated in an olefin splitter overhead stream in an overhead line 38 from a bottoms stream in a bottoms line 40 comprising distillate-range C9+ hydrocarbons, typically C9-C22 olefins. The olefin splitter column 36 may be operated at a bottoms temperature of about 200° C. (400° F.) to about 315° C. (600° F.) and an overhead pressure of about 35 kPa (gauge) (5 psig) to about 420 kPa (gauge) (60 psig). It is envisioned that the olefin splitter column 36 may be two columns.

The olefin splitter overhead stream may be cooled to about 66° C. (150° F.) to about 93° C. (200° F.) and a resulting condensate portion refluxed from an olefin splitter receiver 42 back to the olefin splitter column 36. A net vapor stream in a receiver overhead line 44 from the olefin splitter receiver 42 may be compressed up to oligomerization pressure in an off-gas compressor 46 to provide a light oligomer stream in line 48 either in vapor phase or in liquid phase after cooling. Alternatively, the olefin splitter overhead stream in the overhead line 38 may be fully condensed by cooling perhaps in an external refrigeration loop to provide a liquid light oligomer stream in line 48. The light oligomer stream in line 48 may be split between a light olefin drag stream in line 50 and the oligomer recycle stream in line 26 that may be recycled to the second stage oligomerization reactor 32, but preferably to the first stage oligomerization reactor 22. The light olefin drag stream in line 50 may comprise about 1 to about 15 wt % of the light oligomer stream in line 48. The light oligomer stream in line 48 may comprise about 30 to about 80 wt % light olefins.

In an embodiment, the oligomer recycle stream in line 26 may be mixed with the last oligomerized olefin stream in the last oligomerized effluent line 24d to provide the charge oligomerized olefin stream in line 28 for charge to the second stage oligomerization reactor 32. It is also envisioned that the oligomer recycle stream in line 26 be mixed with the first diluted olefin stream in line 16a or divided up between the first through fourth diluted olefin streams in lines 16a-16d to dimerize or oligomerize unreacted ethylene.

The heavy olefin stream in the splitter bottoms line 40 may be split between a reboil stream that is reboiled and fed back to the olefin splitter column 36 and a heavy olefin stream in a net splitter bottoms line 41. The heavy olefin stream in the net bottoms line 41 is cooled by heat exchange with the oligomerized olefin stream in line 37 and then transported to the hydrogenation section 110 in FIG. 2. The reboil stream in line 51 may be heated by heat exchange with a reboil stream in line 83 from the jet fractionation bottoms line 76 in FIG. 2 which is returned to the jet fractionation column in line 85 in FIG. 2.

Turning to the hydrogenation section 110 in FIG. 2, the heavy olefin stream in the net olefin splitter bottoms line 30 from FIG. 1 comprising distillate-range C9+ oligomerized olefins may be hydrogenated to saturate the olefinic bonds in a hydrogenation reactor 52 to provide fuels. This step is performed to ensure the product motor fuel meets or exceeds the thermal oxidation requirements specified in ASTM D7566-10a for hydroprocessed synthesized paraffinic kerosene (SPK). Additionally, saturating the oligomerized heavy olefins will provide the paraffin stream that may be used as the diluent stream in line 14. The heavy olefin stream in line 30 may be cooled to produce steam and be combined with the light olefin drag stream comprising C2 to C8 olefins in line 50 also from FIG. 1 to produce a combined olefin stream in line 54. The combined olefin stream in line 54 may also be combined with a hydrogen stream in line 56 to provide a combined hydrogenation charge stream in line 58 which is cooled and charged to the hydrogenation reactor 52 at 125° C. (257° F.) to about 315° C. (600° F.) and 3.5 MPa (500 psig) to about 6.9 MPa (1000 psig). An excess of hydrogen may be employed to ensure complete saturation such as about 1.5 to about 2.5 of stochiometric hydrogen.

Hydrogenation is typically performed using a conventional hydrogenation or hydrotreating catalyst, and can include metallic catalysts containing, e.g., palladium, rhodium, nickel, ruthenium, platinum, rhenium, cobalt, molybdenum, or combinations thereof, and the supported versions thereof. Catalyst supports can be any solid, inert substance including, but not limited to, oxides such as silica, alumina, titania, calcium carbonate, barium sulfate, and carbons. The catalyst support can be in the form of powder, granules, pellets, or the like.

In an exemplary embodiment, hydrogenation is performed in the hydrogenation reactor 52 that includes a platinum-on-alumina catalyst, for example about 0.5 wt % to about 0.9 wt % platinum-on-alumina catalyst. The hydrogenation reactor 52 converts the olefins into a paraffin product having the same carbon number distribution as the olefins, thereby forming distillate-range paraffins suitable for use as jet and diesel fuel.

The saturated heavy stream discharged from the hydrogenation reactor 52 in line 60 may be cooled by heat exchange with a saturated heavy liquid stream in a separator bottoms line 66 and fed to a hydrogenation separator 62. In the hydrogenation separator 62, the saturated heavy stream is separated into a hydrogenated separator vapor stream in an overhead line 64 and the saturated heavy liquid stream in the hydrogenation separator bottoms line 66. A purge in line 65 may be taken from the hydrogenated separator vapor stream in line 64 and the remainder may be compressed and combined with make-up hydrogen in line 68 to provide the hydrogen stream in line 56. The saturated heavy liquid stream in the bottoms line 66 may be heated by heat exchange with the saturated heavy stream in line 60 and the diluent stream in line 14 and fed to a jet fractionation column 70. In an embodiment, a hot separator and cold separator system may be substituted for a single hydrogenation separator 62.

The saturated heavy liquid stream in the bottoms line 66 may be fed to the jet fractionation column 70 without undergoing prior stripping in a stripper column. Alternatively, a stripper column may be utilized upstream of the jet fractionation column 70. In the jet fractionation column 70, the saturated heavy liquid stream may be separated into an off-gas stream in an overhead line 80, a green jet stream in a net liquid overhead line 74 and a green diesel stream in a bottoms line 76. The jet fractionation column 70 may be operated at a bottoms temperature of about 316° C. (600° F.) to about 482° C. (900° F.) and an overhead pressure of about 35 kPa (5 psig) to about 350 kPa (50 psig).

The jet fractionation overhead stream in the overhead line 72 may be cooled and a resulting condensate portion is produced in line 79 from a bottom of a receiver 78. A portion of the condensate in line 79 is refluxed back to the jet fractionation column 70 while a jet fuel stream in line 84 is transported to a jet stripper column 90. A net off gas stream comprising C8-hydrocarbons is taken in a receiver overhead line 80 from the jet fractionation receiver 78. Most of the hydrocarbons in the net off gas stream in the receiver overhead line 80 are lighter hydrocarbons and can be used to fuel the reboiler for the jet fractionation column 70 and/or the olefin splitter column 36.

The jet stripper column 90 strips light ends from the jet fuel stream in line 84 and sends them in the overhead line 92 back to the condenser 73 with the jet fractionation overhead stream in line 72. A stripped jet fuel product is taken in the jet stripper bottoms line 94 while a portion is reboiled and fed back to the jet stripper column 90. A jet fuel product stream in line 74 is taken from the stripped jet fuel product in line 94, cooled in the cooler 95 and recovered as jet fuel product. The green jet stream taken in the line 74 comprises kerosene range C9-C17 hydrocarbons and may be cooled and taken as product meeting applicable SPK standards. In an alternative embodiment, the green jet stream may be taken from a side line from the side of the jet fractionation column 70.

The green diesel bottoms stream in the bottoms line 76 may be split between a reboil stream that is reboiled and fed back to the jet fractionation column 70, a green diesel product stream in line 82 and a diluent stream in line 14. The diluent stream in line 14 may be cooled by heat exchange with the separator bottoms line 66 and by steam generation and recycled back to be mixed with the olefin stream in line 12 in the oligomerization section 10 in FIG. 1, preferably the first olefin stream in line 12a, to provide the first diluted olefin stream in line 16a to absorb the exotherm in the first stage oligomerization reactor 22. The green diesel stream in the diluent line 14 is paraffinic, so it will be inert to the 46 oligomerization and hydrogenation reactions to which it may be subject. Both the jet fuel stream in the line 74 and the diesel stream in line 82 can be cooled and fed to their respective fuel pools. The diesel stream will meet ASTM D975 standards for diesel. The reboil stream in line 81 may be diverted in line 83 to the olefin splitter column 70 to reboil the reboil stream in line 51 from the olefin splitter bottoms stream in line 40 in FIG. 1. The cooled reboil stream may be returned in the line 85 and heated in the heater to boiling and returned to the jet fractionation column.

Figure 3:
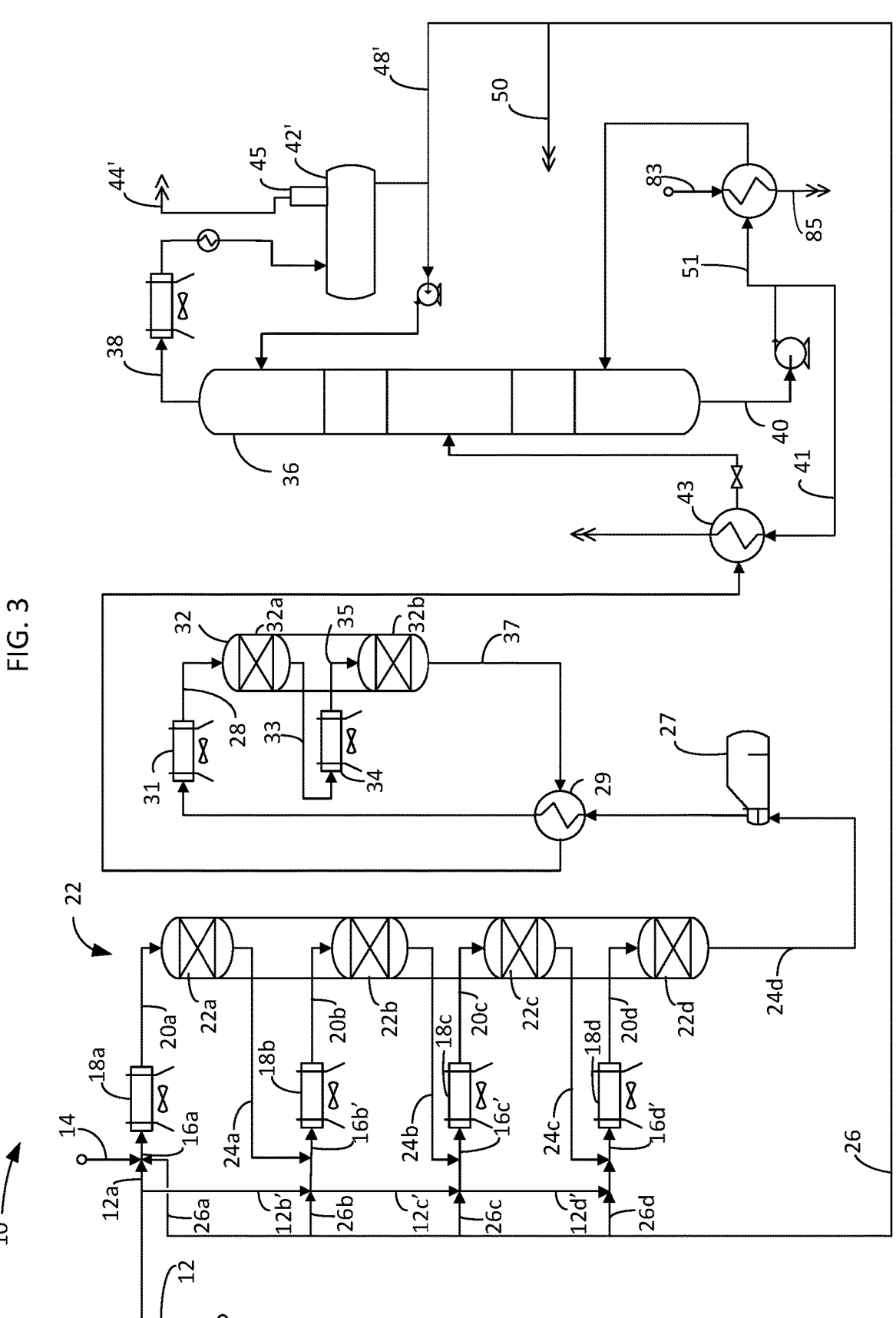
FIG. 3 is a schematic drawing of an alternative embodiment of the oligomerization section of a process and apparatus of FIG. 1.

FIG. 3 shows an embodiment of the oligomerization section 10 which charges the recycle olefin to the upstream first stage oligomerization catalyst beds 22a and 22b. Elements in FIG. 3 with the same configuration as in FIG. 1 will have the same reference numeral as in FIG. 1. Elements in FIG. 3 which have a different configuration as the corresponding element in FIG. 1 will have the same reference numeral but designated with a prime symbol ('). The configuration and operation of the embodiment of FIG. 3 is essentially the same as in FIG. 1 but with the noted exceptions.

A recycle olefin stream in line 26 may be charged to the first stage oligomerization catalyst beds 22a-22d. In an embodiment, the recycle olefin stream is split into multiple recycle olefin streams, first recycle olefin stream in line 26a, a second recycle olefin stream in line 26b, a third recycle olefin steam in line 26c and a fourth recycle olefin stream in line 26d. The flow rates of each recycle olefin stream may be equal or they may be gradated with a greater bias to the upstream beds 26a to 26d or with a greater bias to the downstream beds 26d to 26a. The recycle olefin stream in line 26 may be split into multiple recycle olefin streams in lines 26a to and 26d and fed to respective first stage oligomerization catalyst beds 22a through 22d, respectively.

In an embodiment the first charge olefin stream in line 12a, the diluent stream in line 14 and the first recycle olefin stream in line 26a are mixed to provide a first diluted olefin stream in line 16a', cooled in a first charge cooler 18a to provide a first cooled diluted olefin stream in line 20a and charged to the first, first stage catalyst bed 22a. Ethylene and recycle olefins oligomerize over the first, first stage oligomerization catalyst bed 22a and produce a first oligomerized olefin stream in line 24a that is removed from the first, first stage oligomerized catalyst bed 22a.

A second charge olefin stream in line 12b' may be mixed with the second recycle olefin stream in line 26b and diluted with the first oligomerized olefin stream in line 24a removed from the first, first stage oligomerization catalyst bed 22a to provide a second diluted olefin stream in line 16b'. The first oligomerized olefin stream in line 24a includes the diluent stream from diluent line 14 added to the first olefin stream in line 12a. The second diluted olefin stream in line 16b' may be cooled in a second charge cooler 18b which may be located externally to the first stage oligomerization reactor 22 to provide a second cooled diluted olefin stream in line 20b and charged to a second bed 22b of first stage oligomerization catalyst in a first stage oligomerization reactor 22. The second diluted olefin stream will include diluent and olefins from the first oligomerized olefin stream, the second charge olefin stream and the second recycle olefin stream. The olefins from the first oligomerized olefin stream, the second charge olefin stream and the second recycle olefin stream will further oligomerize in the second catalyst bed 22b. First stage oligomerization of ethylene and olefins in the first oligomerized olefin stream, the second charge olefin stream and the second recycle olefin stream in the second bed 22b of first stage oligomerization catalyst produces a second oligomerized olefin stream in a second oligomerized effluent line 24b at an elevated outlet temperature.

A third charge olefin stream in line 12c' may be mixed with the third recycle olefin stream in line 26c and diluted with the second oligomerized olefin stream in line 24b removed from the second, first stage oligomerization catalyst bed 22b to provide a third diluted olefin stream in line 16c'. The first oligomerized olefin stream in line 24a includes the diluent stream from diluent line 14 added to the first olefin stream in line 12a. The third diluted olefin stream in line 16b' may be cooled in a third charge cooler 18c which may be located externally to the first stage oligomerization reactor 22 to provide a third cooled diluted olefin stream in line 20c and charged to a third bed 22c of first stage oligomerization catalyst in the first stage oligomerization reactor 22. The third diluted olefin stream will include diluent and olefins from the second oligomerized olefin stream, the third charge olefin stream and the third recycle olefin stream. The olefins from the second oligomerized olefin stream, the third charge olefin stream and the third recycle olefin stream will further oligomerize in the third catalyst bed 22c. First stage oligomerization of ethylene and olefins in the second oligomerized olefin stream, the third charge olefin stream and the third recycle olefin stream in the third bed 22c of first stage oligomerization catalyst produces a third oligomerized olefin stream in a third oligomerized effluent line 24c at an elevated outlet temperature.

A fourth charge olefin stream in line 12d' may be mixed with the fourth recycle olefin stream in line 26d and diluted with the third oligomerized olefin stream in line 24c removed from the third, first stage oligomerization catalyst bed 22c to provide a fourth diluted olefin stream in line 16d'. The first oligomerized olefin stream in line 24a includes the diluent stream from diluent line 14 added to the first olefin stream in line 12a. The fourth diluted olefin stream in line 16d' may be cooled in a fourth charge cooler 18d which may be located externally to the first stage oligomerization reactor 22 to provide a fourth cooled diluted olefin stream in line 20d and charged to a fourth bed 22d of first stage oligomerization catalyst in the first stage oligomerization reactor 22. The fourth diluted olefin stream will include diluent and olefins from the third oligomerized olefin stream, the fourth charge olefin stream and the fourth recycle olefin stream. The olefins from the third oligomerized olefin stream, the fourth charge olefin stream and the fourth recycle olefin stream will further oligomerize in the fourth catalyst bed 22c. First stage oligomerization of ethylene and olefins in the fourth charge olefin stream, the third oligomerized olefin stream and the fourth recycle olefin stream in the fourth bed 22c of first stage oligomerization catalyst produces a fourth oligomerized olefin stream in a fourth oligomerized effluent line 24d at an elevated outlet temperature.

In an embodiment illustrated in FIG. 3, a splitter overhead stream in a splitter overhead line 38' from the olefin splitter column 36' may be cooled to full condensation perhaps in an external refrigeration loop and fed to an olefin splitter receiver 42'. A vent stream in line 44' from the receiver 42' may be equipped with a condenser chiller 45 to ensure full condensation. Condensate from the olefin splitter receiver 42' may provide a reflux to the column and a light oligomer stream in line 48'. The light oligomer stream in line 48' may be split between a light olefin drag stream in line 50 and the oligomer recycle stream in line 26 that may be recycled to the second stage oligomerization reactor 32, but preferably to the first stage oligomerization reactor 22. The light olefin drag stream in line 50 may comprise about 1 to about 15 wt % of the light oligomer stream in line 48'. The light oligomer stream in line 48 may comprise about 30 to about 80 wt % light olefins.

With these exceptions, the embodiment of FIG. 3 operates and is arranged as the embodiment in FIG. 1.

Starting with ethylene, the disclosed process can efficiently produce green jet fuel and green diesel fuel that meets applicable fuel requirements while managing exothermic heat generation. Carbon recovery in the process can exceed 95%.

EXAMPLE

Figure 4:
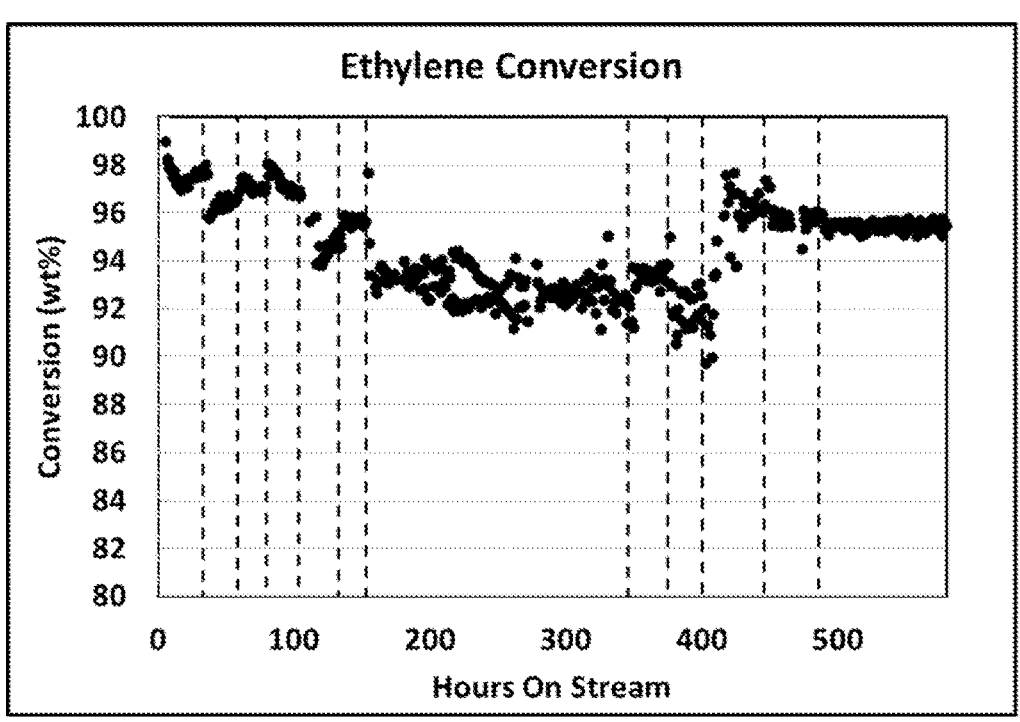
FIG. 4 is a plot of ethylene conversion over time.
Figure 5:
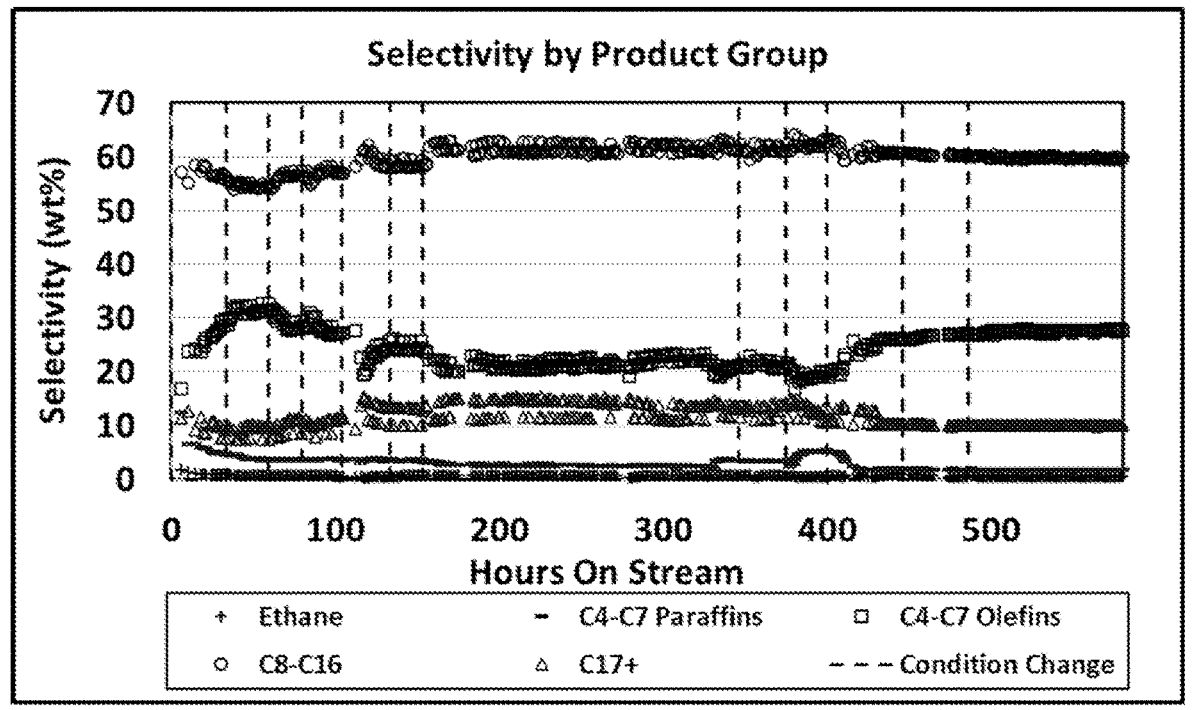
FIG. 5 is a plot of product selectivity over time.

A first stage oligomerization catalyst comprising MTT zeolite and a second stage oligomerization catalyst comprising nickel on amorphous silica alumina catalyst were loaded in a pilot plant reactor in stacked bed configuration. The reactor was fed with ethylene, light paraffin diluent, and was operated in a recycle mode to fully utilize light olefins. The test was conducted at 6.2 MPa (gauge) (900 psig) pressure, with an inlet temperature to the first oligomerization stage catalyst varying from 210 to 250° C. and to the second oligomerization stage catalyst varying from 130 to 170° C. and WHSV in the fresh ethylene charge varying from 0.5 to 1.0 hr$^{-1}$. Depending on the test conditions, the results demonstrate over 90 wt % ethylene conversion shown in FIG. 4 and high jet range selectivity in FIG. 5.

SPECIFIC EMBODIMENTS

While the following is described in conjunction with specific embodiments, it will be understood that this description is intended to illustrate and not limit the scope of the preceding description and the appended claims.

A first embodiment of the disclosure is a process for oligomerizing an olefin stream comprising oligomerizing the olefin stream with a first stage oligomerization catalyst comprising a solid acid catalyst to produce an oligomerized olefin stream; oligomerizing the oligomerized olefin stream with a second stage oligomerization catalyst comprising a metal to provide an oligomerate stream. An embodiment of the disclosure is one, any or all of prior embodiments in this paragraph up through the first embodiment in this paragraph wherein the first stage oligomerization catalyst is a zeolite catalyst. An embodiment of the disclosure is one, any or all of prior embodiments in this paragraph up through the first embodiment in this paragraph wherein the zeolite is an acidic catalyst. An embodiment of the disclosure is one, any or all of prior embodiments in this paragraph up through the first embodiment in this paragraph wherein the zeolite catalyst is an MTT catalyst. An embodiment of the disclosure is one, any or all of prior embodiments in this paragraph up through the first embodiment in this paragraph wherein the second stage oligomerization catalyst is a metal catalyst. An embodiment of the disclosure is one, any or all of prior embodiments in this paragraph up through the first embodiment in this paragraph wherein the metal catalyst is a nickel catalyst. An embodiment of the disclosure is one, any or all of prior embodiments in this paragraph up through the first embodiment in this paragraph wherein oligomerizing with the first stage oligomerization catalyst is conducted in multiple catalyst beds. An embodiment of the disclosure is one, any or all of prior embodiments in this paragraph up through the first embodiment in this paragraph further comprising splitting the olefin stream into multiple charge olefin streams and charging each of the multiple charge olefin streams to one of the multiple catalyst beds. An embodiment of the disclosure is one, any or all of prior embodiments in this paragraph up through the first embodiment in this paragraph further comprising mixing a diluent stream with the olefin stream. An embodiment of the disclosure is one, any or all of prior embodiments in this paragraph up through the first embodiment in this paragraph further comprising mixing a diluent stream with the multiple charge olefin streams.

A second embodiment of the disclosure is a process for oligomerizing an olefin stream comprising oligomerizing a charge olefin stream and a recycle olefin stream with a first stage oligomerization catalyst to produce a first oligomerized olefin stream; oligomerizing the first oligomerized olefin stream with a first stage oligomerization catalyst to produce a second oligomerized olefin stream; oligomerizing the second oligomerized olefin stream with a second stage oligomerization catalyst to provide an oligomerate stream; and taking the recycle olefin stream from the oligomerate stream. An embodiment of the disclosure is one, any or all of prior embodiments in this paragraph up through the second embodiment in this paragraph further comprising oligomerizing the first oligomerized olefin stream and a recycle olefin stream with the first stage oligomerization catalyst to produce the second oligomerized olefin stream.

A third embodiment of the disclosure is a process for oligomerizing an olefin stream comprising oligomerizing a charge olefin stream with a first stage oligomerization catalyst to produce a first oligomerized olefin stream; oligomerizing the first oligomerized olefin stream and a recycle olefin stream with a first stage oligomerization catalyst to produce a second oligomerized olefin stream; oligomerizing the second oligomerized olefin stream with a second stage oligomerization catalyst to provide an oligomerate stream; and taking the recycle olefin stream from the oligomerate stream. An embodiment of the disclosure is one, any or all of prior embodiments in this paragraph up through the third embodiment in this paragraph further comprising splitting a charge olefin stream into a first charge olefin stream and a second charge olefin stream and oligomerizing the second charge olefin stream with the first oligomerized olefin stream and the recycle olefin stream. An embodiment of the disclosure is one, any or all of prior embodiments in this paragraph up through the third embodiment in this paragraph further comprising diluting the first charge olefin stream with a diluent stream before oligomerizing the first charge olefin stream. An embodiment of the disclosure is one, any or all of prior embodiments in this paragraph up through the third embodiment in this paragraph further comprising splitting the charge olefin stream into multiple charge olefin streams including the first charge olefin stream and the second charge olefin stream and charging the first charge olefin stream of the multiple charge olefin streams to an upstream first stage oligomerization reactor. An embodiment of the disclosure is one, any or all of prior embodiments in this paragraph up through the third embodiment in this paragraph further comprising splitting the recycle olefin stream into multiple recycle olefin streams including a first recycle olefin stream and a second recycle olefins stream and charging the first recycle olefin stream of the multiple recycle olefin streams to a downstream first stage oligomerization reactor. An embodiment of the disclosure is one, any or all of prior embodiments in this paragraph up through the third embodiment in this paragraph further comprising charging the first charge olefin stream of the multiple charge olefin streams to a first, first stage oligomerization reactor and the second charge olefin stream of the multiple charge olefin streams to a second, first stage oligomerization reactor. An embodiment of the disclosure is one, any or all of prior embodiments in this paragraph up through the third embodiment in this paragraph further comprising charging the first recycle olefin stream of the multiple recycle olefin streams to a third first stage oligomerization reactor and the second recycle olefin stream of the multiple recycle olefin streams to a fourth first stage oligomerization reactor. An embodiment of the disclosure is one, any or all of prior embodiments in this paragraph up through the third embodiment in this paragraph wherein taking the recycle olefin stream from the oligomerate stream comprises fractionating the oligomerate stream to provide an overhead stream comprising the recycle olefin stream. Without further elaboration, it is believed that using the preceding description that one skilled in the art can utilize the present disclosure to its fullest extent and easily ascertain the essential characteristics of this disclosure, without departing from the spirit and scope thereof, to make various changes and modifications of the disclosure and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for oligomerizing an olefin stream comprising:

oligomerizing said olefin stream with a first stage oligomerization catalyst comprising a solid acid catalyst to produce an oligomerized olefin stream;

oligomerizing said oligomerized olefin stream with a second stage oligomerization catalyst comprising an amorphous silica-alumina base with a metal to provide an oligomerate stream.

2. The process of claim 1 wherein said first stage oligomerization catalyst is a zeolite catalyst.

3. The process of claim 2 wherein said zeolite has a framework having a ten-ring pore structure.

4. The process of claim 3 wherein said zeolite catalyst is an MTT catalyst.

5. The process of claim 1 wherein said metal is selected from either Group VIII and/or Group VIB in the periodic table.

6. The process of claim 5 wherein said metal catalyst is a nickel catalyst.

7. The process of claim 1 wherein oligomerizing with said first stage oligomerization catalyst is conducted in multiple catalyst beds.

8. The process of claim 7 further comprising splitting said olefin stream into multiple charge olefin streams and charging each of said multiple charge olefin streams to one of said multiple catalyst beds.

9. The process of claim 1 further comprising mixing a diluent stream with said olefin stream.

10. The process of claim 8 further comprising mixing a diluent stream with said multiple charge olefin streams.

* * * * *